United States Patent
Hicks et al.

(12) 
(10) Patent No.: US 6,348,346 B1
(45) Date of Patent: *Feb. 19, 2002

(54) METHOD OF INHIBITING BINDING ACTIVITY OF IMMUNOGLOBULINS

(75) Inventors: Clair L. Hicks, Lexington, KY (US); Zeynep Ustunol, Holt, MI (US)

(73) Assignee: University of Kentucky Research Foundation, Lexington, KY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/799,281

(22) Filed: Feb. 13, 1997

Related U.S. Application Data (63) Continuation-in-part of application No. 08/250,245, filed on May 27, 1994, now abandoned.

(51) Int. Cl.$^7$ ................................................. C12N 1/38
(52) U.S. Cl. ................. 435/244; 435/253.6; 435/252.9; 435/68.1
(58) Field of Search ...................... 435/244, 41, 253.6, 435/252.9, 68.1

(56) References Cited

U.S. PATENT DOCUMENTS

| | | | | |
|---|---|---|---|---|
| 4,001,437 A | * | 1/1977 | Jacggi | 426/34 |
| 4,220,723 A | * | 9/1980 | Eckmayer | 435/265 |
| 4,293,571 A | * | 10/1981 | Olotsson | 426/7 |
| 4,427,658 A | | 1/1984 | Maubois et al. | |
| 4,436,724 A | | 3/1984 | Ohnishi et al. | |
| 4,918,008 A | * | 4/1990 | Gauri | 435/68.1 |
| 5,039,532 A | * | 8/1991 | Jost | 426/41 |
| 5,099,005 A | | 3/1992 | Nichols et al. | |
| 5,135,869 A | | 8/1992 | Kaneko et al. | |
| 5,185,321 A | | 2/1993 | Link et al. | |
| 5,324,515 A | * | 6/1994 | Lee | 424/115 |

OTHER PUBLICATIONS

Gilliespie; Medical Microbiology Illustrated; Butterworth; 1994; 253–4.

Gillespie, SH., In "Medical Microbiology Illustrated", p. 253–254, Butterworth, 1994*

Sultan et al., Ann Agric Sci (Cairo) 30 (2). 1985 (Recd. 1986). 1211–1224.*

Champagne et al., Can. J. Ind. Microbiol. (1991), 7(2), 147–9.*

Fayed et al., Egypt J Food Sci 14 (2). 1986 (Recd. 1987). 313–322.*

* cited by examiner

*Primary Examiner*—Irene Marx
(74) *Attorney, Agent, or Firm*—King and Schickli PLLC (57) ABSTRACT

A method for inhibiting culture agglutination in a fermentation medium including immunoglobulins includes the step of treating a source of immunoglobulins with an enzyme, such as papain, ficin, bromelain and mixtures thereof to hydrolyze the immunoglobulins into immunoreactive peptides having a molecular weight of less than 10,000 Daltons. This is accomplished utilizing ultrafiltration and/or diafiltration techniques. Next, is the collecting of peptides so produced and the adding of the peptides to a growth media for microorganisms useful in fermenting the fermentation medium. This is followed by growing the microorganisms in the inoculated growth media and adding the microorganisms grown in the treated growth media to the fermentation medium. A method for inhibiting the binding activity of mammalian immunoglobulins with an immunogen and inhibitors of the binding activity of immunoglobulins are also disclosed and claimed.

6 Claims, 3 Drawing Sheets

METHOD OF INHIBITING BINDING ACTIVITY OF IMMUNOGLOBULINS

This is a continuation-in-part of U.S. patent application Ser. No. 08/250,245 now abandoned, filed May 27, 1994.

TECHNICAL FIELD

The present invention relates generally to the field of biotechnology and, particularly, to a method for inhibiting the binding activity of immunoglobulins with immunogens, a method for inhibiting culture agglutination and the actual inhibitors.

BACKGROUND OF THE INVENTION

Many forms of immune proteins exist in mammals including humans, and other classes of animals having immune systems. It is generally believed that the immune proteins IgM and IgG are the most important proteins that provide protection against microbial invasion of mammals. IgM is similar to IgG but is composed of five IgG-like molecules in a pentamer arrangement. The immunoglobulins IgM and IgG are circulated in the blood to combat invasion by foreign matter, mainly bacteria and are transferred to milk to establish immunity in nursing offspring.

Scientific literature suggests that the immune proteins IgM and IgG interact when a binding site on the variable regions of the light and heavy chains (see FIG. 1) attaches to an antigenic site or to a complimentary binding site on the tail of the heavy chain (Fc fraction) of another IgM or IgG molecule. Many researchers believe that IgM and IgG lose their interactive ability when the heavy chains are removed from the Fab fractions. Our work in the development of the present invention, however, indicates that the carbohydrate moieties or constant regions on both the light and heavy chains of immune proteins are capable of interacting with antigenic sites and/or bridging compounds thereby causing immune reactions and agglutination. Thus, it should be appreciated, that simple cleavage of the Fab fraction is not effective to inhibit immune reactions. Accordingly, a new method must be developed to achieve this end.

SUMMARY OF THE INVENTION

Accordingly, it is a primary object of the present invention to provide a method for inhibiting the binding activity of immunoglobulins with immunogens. Such a method has a number of beneficial applications including, but not limited to, inhibiting culture agglutination in a fermentation medium and blocking selected antigenic sites so as to prevent problematic immune reactions in the health care field.

Yet another object of the present invention is to provide a method for inhibiting culture agglutination in a fermentation medium wherein agglutination of the microorganisms responsible for fermentation is substantially prevented. Such a method allows, for example, more efficient production of a more consistent and higher quality fermentation product (e.g. cheddar cheese, cottage cheese).

Still another object of the present invention is to provide a method for inhibiting the binding activity of mammalian immunoglobulins and in particular IgA, IgG and IgM in a biologically safe and effective manner. Such an approach may be utilized to limit or prevent immune reactions and prevent infection and, accordingly, are beneficial for a number of uses in the care and treatment of patients suffering from a number maladies.

Yet another object of the present invention is to provide inhibitors of the binding activity of immunoglobulins including mammalian immunoglobulins and particularly IgA, IgG and IgM. This is accomplished through the utilization of corresponding immunoglobulins hydrolyzed with plant proteases to provide peptides having a molecular weight of less than 10,000 Daltons and preferably of about 1,000 Daltons.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an improved method is provided for inhibiting the binding activity of immunoglobulins with immunogens. The method is particularly adapted for utilization in inhibiting the binding activity of mammalian immunogens including, specifically, IgA, IgG and IgM immune proteins. The method broadly includes the initial step of treating a source of immunoglobulins with an enzyme that hydrolizes the immunoglobulins into immunoreactive peptides having a molecular weight of less than 10,000 Daltons. Preferably, the enzyme is a plant protease that cleaves the immunoglobulins, IgA, IgG and IgM, above the second disulfide bond (see FIG. 1). This results in the liberation of two Fab fractions. The enzymes papain, ficin and bromelain are particularly useful for this purpose.

In addition to cleaving the immunogens IgA, IgG and IgM above the second disulfide bond, the hydrolysis is continued for an additional period of time to clip and remove the carbohydrate moiety or constant regions from the variable regions so as to provide a peptide fraction having a molecular weight of less than 10,000 Daltons. This may be accomplished through ultrafiltering the source of immunoglobulins as they are hydrolized with the enzyme. A diafiltration technique may be utilized so that the smaller peptide fractions produced as a result of hydrolysis (i.e. those under 10,000 Daltons) pass as permeate through a polysulfone or other membrane having a molecular weight cut off of 10,000 Daltons. Specifically, to achieve this end, hydrolysis preferably is completed at a temperature between 30–50° C. for a period of at least two hours. As permeate is removed from the source of immunoglobulins undergoing hydrolysis a buffer of equivalent volume may be added.

The permeate, consisting of peptides of a molecular weight of less than 10,000 Daltons and preferably approximately 1,000 Daltons is then collected. Following collecting is the reacting of immunogens with the peptides so as to bind and block antigenic sites on the immunogens. Then follows the introducing of the peptide bound and blocked immunogens into the mammal. Advantageously, the bound and blocked antigenic sites on the immunogens make the immunogens substantially "invisible" to the immune system of the mammal thereby preventing undesired and problematic immune reactions from occurring.

Such an approach has a number of applications including, specific use in the artificial insemination of mammals including humans and other animals. Specifically, the sperm cells to be inseminated are reacted with the peptide so as to bind and block the antigenic sites or determinants on the sperm cells. When subsequently inseminated into a recipient, the immune reaction of the recipient is reduced and/or substantially eliminated, and accordingly, the aggregation of sperm cells is virtually prevented. Thus, the sperm cells remain free to reach the ovum for purposes of fertilization.

In accordance with yet another aspect of the present invention, a method for inhibiting culture agglutination in a fermentation medium including immunogens is provided. As before, this method includes an initial step of treating a source of immunoglobulins with an enzyme such as a plant protease to hydrolize the immunoglobulins into peptides having a molecular weight of less than 10,000 Daltons and preferably, approximately 1,000 Daltons. Specifically, as previously described these peptides are produced utilizing ultrafiltration and diafiltration techniques. Preferably, papain, ficin and/or bromelain is used as the enzyme.

The immunoglobulins may be obtained from a number of sources including, but not limited to, raw whey, dry whey, whey protein isolates, non-fat-dried milk, blood serum protein isolates, purified immunogen preparations and mixtures thereof.

Following hydrolysis is the collecting of the peptides produced as a result of the treatment of the immunoglobulins with papain, ficin and/or bromelain and in accordance with the ultrafiltration and diafiltration techniques. Specifically, the resulting peptides present in the permeate may be concentrated utilizing reverse osmosis or evaporation and then dried using freeze drying, spray drying or vacuum drying techniques. These dried preparations can then be formulated into existing culture media preparations.

The peptides in these culture media preparations are then utilized by inoculating a growth media for microorganisms, useful in fermenting the fermentation medium, with the peptides. Next is the growing of the microorganisms in the inoculated growth media whereby the peptides bind antigenic sites on the microorganisms. This is then followed by adding the microorganisms grown in the inoculated growth media to the fermentation medium whereby the peptide bound antigenic sites on the microorganisms block the immunoglobulins in the fermentation medium from binding those antigenic sites and thereby causing agglutination of the microorganisms.

Such a method is particularly useful in the production of cottage, cheddar and other cheeses wherein agglutination is a significant problem leading to revenue loss. Specifically, agglutination results in uneven distribution of starter culture throughout the milk and uneven acid production in the cheese vat. Grainy, shattered curd, sediment formation and slow acid production are all problems that directly relate to agglutination of lactic acid starter strains. Accordingly, direct consequences of agglutination are inconsistent product quality and yield losses which both lead to decreased profits. Accordingly, as the present invention addresses and largely relieves the agglutination problem, it represents a significant advance in the art.

In accordance with still another aspect of the present invention, an inhibitor is provided for inhibiting the binding activity of immunoglobulins and particularly mammalian immunoglobulins including IgA, IgG and IgM. Specifically, the inhibitor is derived from a source of immunoglobulins hydrolized with a plant protease such as papain, ficin and/or bromelain and then ultrafiltered with or without diafiltering to provide peptides having a molecular weight of less than 10,000 Daltons and preferably approximately 1,000 Daltons. Such an inhibitor will have a number of unique biotechnological applications such as in the health care field where it is particularly desirable to block problematic immune reactions.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of this specification, illustrates several aspects of the present invention, and together with the description serves to explain the principles of the invention. In the drawing.

Reference will now be made in detail to the present preferred embodiment of the invention, an example of which is illustrated in the accompanying drawing.

DETAILED DESCRIPTION OF THE INVENTION

A method for inhibiting the binding activity of immunoglobulins and, particularly mammalian immunoglobulins IgA, IgM and IgG with an immunogen will now be described in detail. The method includes the initial step of treating mammalian immunoglobulins including IgA, IgG and IgM with an enzyme that hydrolizes the immunoglobulins into immunoreactive peptides having a molecular weight of less than 10,000 Daltons. Any source of immunoglobulins may be utilized including, for example, raw whey, dry whey, whey protein isolates, non-fat-dried milk, blood serum protein isolates, pure fat immune protein preparations and mixtures thereof. It should be appreciated, however, that this list is not exclusive and that other sources of immunoglobulins can be utilized.

Figure 1:
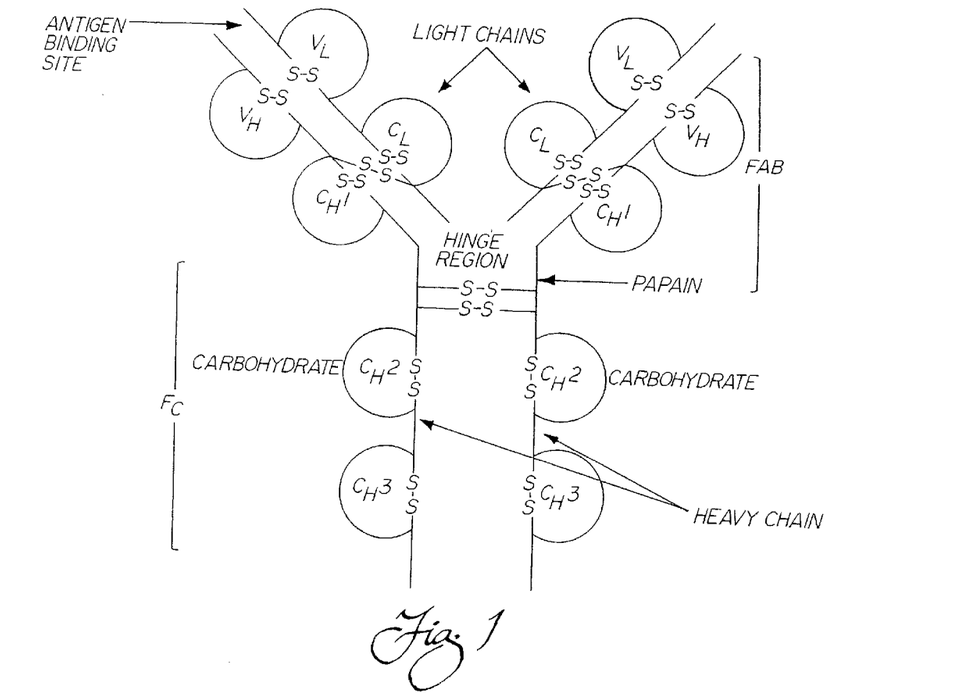
FIG. 1 is a schematical representation of an IgG molecule.

Preferably, the enzyme utilized cleaves the IgA, IgG and the IgM above the second disulfide bond (see FIG. 1). Accordingly, plant proteases such as papain, ficin and bromelain are particularly useful enzymes for purposes of the method of the present invention. Other enzymes such as trypsin, chymotrypsin and pepsin fail to provide the desired cleavage above the second disulfide bond and, accordingly, are not appropriate for utilization in the present method.

More particularly, the production of the desired peptides is completed in accordance with ultrafiltering with or without diafiltering techniques. Preferably, the source of immunoglobulins being treated with the enzyme is ultrafiltered through a polysulfone or other membrane having a molecular weight cutoff of 10,000 Daltons. The permeate, that is, the material passing through the membrane, comprises peptides having a molecular weight of less than 10,000 Daltons. Included in this are the carbohydrate moieties clipped from the light chains and variable regions of the IgA, IgG and IgM molecules. In fact, peptides having a molecular weight of slightly greater than 1,000 Daltons have been found to provide the greatest inhibitory activity relative to the binding of immunoglobulins with antigen sites. Peptides smaller than 1,000 Daltons generally exhibit less activity and, therefore, are of little interest relative to the present method.

As the peptide permeate is collected, an appropriate buffer (e.g. pasteurized skim milk) may be added to the source of immunoglobulins being treated with the enzyme. This is done volume-for-volume so that the original volume of the immunoglobulin source and enzyme (i.e. the retentate) is substantially maintained at a given level.

The enzymatic treatment of the immunoglobulins is completed at any temperature where enzymatic inactivation does not occur. However, temperatures just below the enzyme's point of denaturation are most efficient. Accordingly, for papain, ficin and bromelain the enzymatic treatment is completed between 30–50° C. and most preferably approximately 40° C. Further, the enzymatic treatment is completed for a relatively extended period of time of at least two hours. This allows the enzyme to hydrolize significant portions of the immune proteins IgA, IgG and IgM including the constant regions and carbohydrate moieties of the variable regions and light chains. Of course, as the small peptides are cleaved, they are washed through the ultrafiltration membrane as permeate.

As indicated above, the permeate from the ultrafiltration comprises peptides of less than 10,000 Daltons and preferably, peptides of approximately 1,000 Daltons. Following collection, these may be concentrated utilizing reverse osmosis or evaporation in accordance with procedures well known in the art. These peptides may then be dried by using freeze drying, spray drying, or vacuum drying techniques also well known to those skilled in the art. These dried preparations may then be subsequently formulated into usable preparations for any number of applications.

In accordance with further aspects of the method for inhibiting the binding activity of mammalian immunoglobulins, the next step is the reacting of an immunogen with the peptides produced and collected in the manner just described. These peptides then bind and block antigenic sites/determinants on the immunogens. This may be done in accordance with any number of ways appropriate to achieve this purpose. For example, where spermatozoa are being treated for purposes of subsequent artificial insemination, the spermatozoa may be diluted by adding an appropriate quantity of physiologically balanced sodium citrate solution maintained at an appropriate temperature to maintain the viability of the spermatozoa. The inhibitory peptides are then added to the spermatozoa solution which may be suitably mixed by agitation for a period of approximately 15 minutes.

Following the reacting of the immunogen with the peptides is the step of introducing the peptide bound and blocked immunogen (e.g. spermatozoa) into the mammal. Since the antigenic sites are bound and blocked, the natural antibody defense network of the mammal is essentially prevented from reacting and attacking the immunogen. Accordingly, problematic immune reactions may be essentially defeated. Thus, it should be appreciated that this invention has potentially unlimited applications in the health care field where problematic immune reactions might otherwise prevent a medical doctor or technician from completing treatment and achieving a desired result. For example, in the instance of artificial insemination, a greater number of spermatozoa are maintained viable through inhibition of the binding activity of the immunoglobulins of the female host. Accordingly, these spermatozoa remain free to reach the ovum and complete the desired fertilization.

In accordance with yet another aspect of the present invention a method is provided for inhibiting culture agglutination in a fermentation medium including immunoglobulins. As previously described, the method includes the initial step of treating a source of immunoglobulins with an enzyme (e.g. papain, ficin and/or bromelain) to hydrolize the immunoglobulins into peptides having a molecular weight of less than 10,000 Daltons. The ultrafiltration and diafiltration techniques already described are utilized for this purpose. Similarly, the collecting of the peptides and the concentrating and drying of the peptides for subsequent formulation into culture media preparations is also completed. These peptides, preferably, of approximately 1,000 Daltons and incorporating carbohydrate moieties clipped from tips of the light chains or variable regions of IgA, IgG and IgM immune proteins function to inhibit the binding activity of immunoglobulins.

The next step in the method of inhibiting culture agglutination is the adding of the peptides to a growth media for microorganisms useful in fermenting the fermentation medium. Specifically, the peptides are mixed with the growth media at a weight ratio of peptides to microorganisms of at least substantially between 0.05 to 1 and 0.2 to 1. Microorganisms are then added to and grown in the inoculated growth media for a period of time of generally between 3 and 24 hours while maintaining the growth media within a temperature range necessary to promote growth and maintain the viability of the microorganisms. Preferably, some mixing is provided, such as with internal pH controlled growth media through, for example, slow agitation or other means. As the microorganisms grow in the inoculated growth media, the peptides bind to antigenic sites or determinants on the microorganisms.

Following growth, the microorganisms may be used directly or recovered as, for example, by means of centrifugation in a manner known in the art. Next is the adding of the microorganisms grown in the inoculated growth media to the fermentation medium. There the microorganisms remain free to promote fermentation. Specifically, bound and blocked antigenic sites prevent immunoglobulins in the fermentation medium (e.g. whey or milk culture) from binding with the microorganisms and agglutinating microorganisms to form long chains or clumps that entrap acid coagulated casein and settle to the bottom of the vat.

As a result of the method of the present invention, agglutination is significantly reduced and/or substantially eliminated. This results in an improved and more consistent distribution of microorganisms or starter culture throughout the fermentation medium and a more even acid production in the vat. Accordingly, product quality is more consistent and yield losses are reduced to the economic benefit of the manufacturer.

The following example is presented to further illustrate the invention, but it is not to be considered as limited to.

EXAMPLE 1

Cultures:

Frozen commercial *Lactococcus lactis* bulk starter cultures OS, M30 and M37 (Rhone-Pôulenc/Marschall Div., Madison, Wis.) were inoculated (0.1 g) into 10 mL aliquot of reconstituted NFDM (10% wt/vol) which had been sterilized. The tubes were incubated at 26° C. for approximately 3 hours or until a curd was formed. In the second propagation the formed curd was transferred into 100 mL of sterilized NFDM (10% wt/vol) and incubated for 18 hours. 10 milliliters of the second propagation was transferred into enzyme treated and control media, prepared as described below and incubated.

Commercial cultures OS, M30 and M37 were selected because of their sensitivities to agglutination. The OS culture is a cottage cheese culture which does not normally agglutinate. This culture was used as a control in the experimental design. Cultures M30 and M37 are cheddar cheese cultures that are extremely sensitive to agglutination. These two cultures represent a worst case scenario if used in the manufacture of cottage cheese.

Media Preparation:

Rennet whey was treated with papain (Sigma Chemical Co., St. Louis, Mo.) while being ultrafiltered and diafiltered using a hollow fiber membrane (Supelco, Bellefonte, Pa.) with a molecular weight cut-off of 10,000 Daltons. The process ran for 2 hours at 40° C. The permeate was collected and freeze dried. The freeze dried permeate was added (at 41.7% level, dry weight basis) to an internal pH control buffer salt mixture (as described in U.S. Pat. No. 4,402,986) (Galloway West, Wis.) to replace the whey. A control media was prepared using untreated whey. Both media were reconstituted (75.7 g/L) split into three fractions and heat treated at 85° C. for 45 minutes. The media were cooled to 26° C. and inoculated with the test cultures and incubated at 26° C. for 16 hours or until pH 5.3 was achieved.

Monitoring Agglutination:

Culture agglutination was monitored by determining the pH differential in skim milk and by direct microscopic examination. Agglutination in skim milk was monitored by inoculating the fermented media at a 5% level into pasteurized (63° C., 30 minutes) skim milk contained in 1000 mL graduated cylinders and incubated at 32° C. The pH differential was determined by measuring top and bottom pH of skim milk in the graduated cylinders at 1 hour intervals over 5 hours. Recordings were made 5 centimeters below the skim milk surface and at the bottom of the cylinder. A pH meter (American Scientific Products, McGaw Park, Ill.) was equipped with an Orion combination pH electrode (Orion Research, Inc., Boston, Mass.). The electrode was attached to a stainless steel rod, which was used to lower the electrode to the bottom of the cylinder. A pH differential was computed by subtracting bottom pH from the top pH.

At the end of 5 hours of incubation the bottom of the graduated cylinders were visually inspected for sediment formation. Differences in total solids between top and bottom of the cottage cheese vats is a sensitive indicator of agglutination. Milk (or curd) samples were taken from the bottom of the cylinders and stored at 4° C. overnight for direct microscopic examination the following day. Next day samples were gram stained in accordance with the procedure described in Wu, W. G. Ed. 1986. Stains and Media. Page 33, Medical Microbiology: A Laboratory Study. Star Publication Company, Bellemont Calif., in order to determine culture growth characteristics and cells per chain distribution by microscopic examination. Photomicrographs (1000x) were prepared to illustrate the differences in culture growth characteristics, the extent of chain formation and clumping between the cultures grown in the two media.

Statistical Analysis:

The experiment was replicated four times in a randomized complete block design. Data was analyzed using the general linear model procedure of Statistical Analysis System to determine differences between media on agglutination. Least squares means and significance of each treatment were computed using Type IV sums of squares and predicted difference procedure. Least significant differences were computed for top and bottom pH differential. A pH differential between top and bottom pH of 0.12 units or greater was significant (P<0.05). This pH differential was used as an indicator of starter culture agglutination.

Culture Performance:

Slow or uneven acid production has been reported as an indicator of culture agglutination in previous studies. In this study acid production was also used as an indicator of agglutination, thus an indicator of culture performance. Culture performance over the 5 hour incubation period in skim milk improved (P<0.01) for all three commercial cultures studied (OS, M30 and M37) when grown in enzymically treated whey medium compared to the control (untreated whey) medium (Table 1).

TABLE 1

Effect of enzymically treated whey internal pH control media on rate of acid development in skim milk.

| | | | Culture | | |
|---|---|---|---|---|---|
| | Media | | OS | M30 | M37 |
| Top pH | 1. | Control | 5.25[1] | 6.23 | 6.22 |
| | 2. | Enzyme treated | 5.26 | 5.40 | 5.81 |
| Bottom pH | 1. | Control | 5.10 | 5.55 | 5.57 |
| | 2. | Enzyme treated | 5.17 | 5.08 | 5.63 |
| pH diff.[2] | 1. | Control | 0.15 | 0.68 | 0.64 |
| | 2. | Enzyme treated | 0.09 | 0.31 | 0.18 |

[1]Least square means. Reps = 4 for all treatments, n = 20. A least square difference of 0.12 was calculated when P = 0.05.
[2]pH differential = top pH − bottom pH

Figure 2:
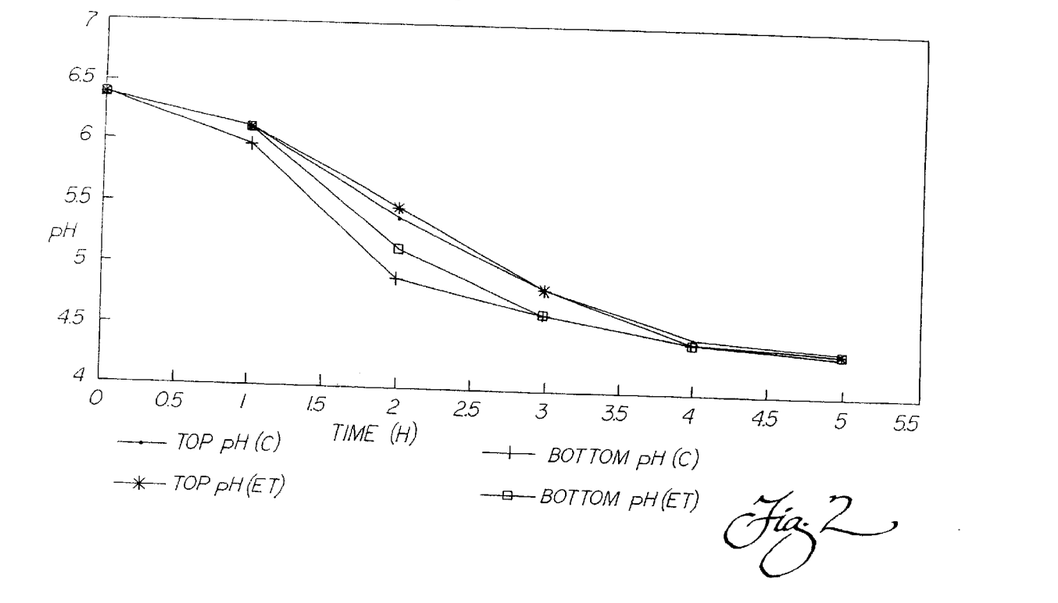
FIG. 2 graphically shows the rate of top and bottom pH decrease of OS culture.

[1]Least square means. Reps=4 for all treatments, n=20. A least square difference of 0.12 was calculated when P=0.05.
[2]pH differential=top pH−bottom pH The OS culture, which is a mixed strain culture that infrequently agglutinates in agglutinin rich milk or under normal conditions, showed the least (P<0.01) amount of culture agglutination when grown in the media. These results were expected. The OS culture during the 5 hours of incubation had a faster rate of acid development (decrease in pH) (P<0.01) (see FIG. 2 and Table 1) and a smaller pH differential (P<0.01) (Table 1) than M30 and M37 cultures (see also FIGS. 3 and 4 and Table 1). Skim milk inoculated with OS culture grown in control or enzymically treated media and incubated had a similar rate of acid production (rate of pH decrease) at the top and bottom of the graduated cylinders. The pH decreased steadily up to 4 hours of incubation and leveled off at pH 4.5 when the skim milk coagulated (FIG. 2). However, over the 5 hour incubation period the pH differentials were lower for culture incubation enzymatically treated whey medium suggesting that the performance of the OS culture was improved by 40%. The pH differentials were 0.15 and 0.09 for enzyme treated and control media, respectively (Table 1). When the skim milk cylinders were visually inspected at the end of 5 hours, no visual sedimentation was observed in either cylinder.

Figure 3:
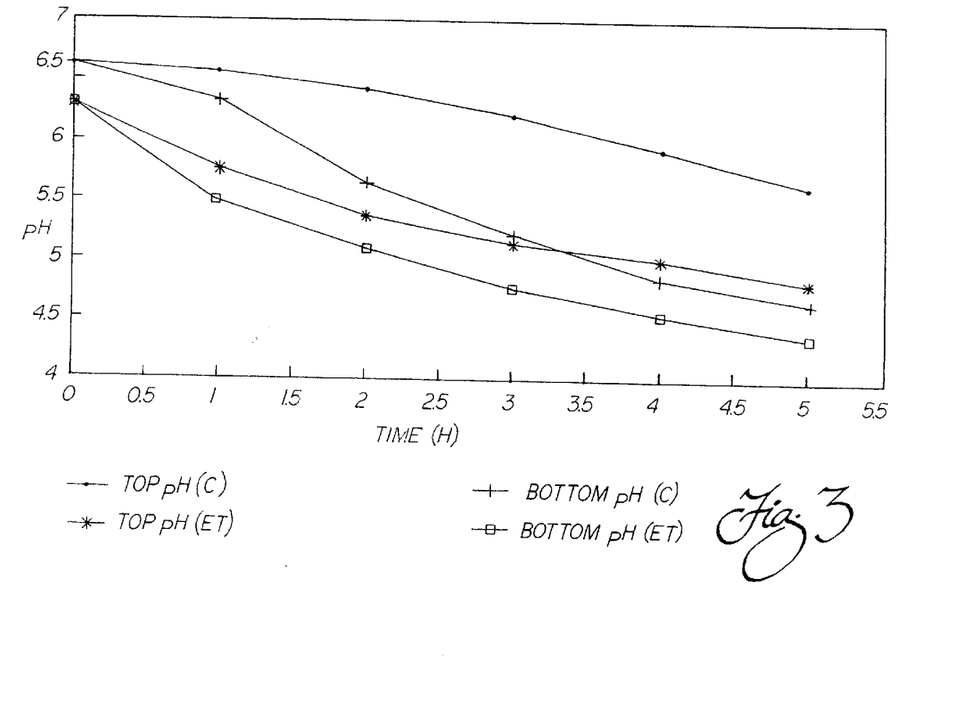
FIG. 3 graphically shows the rate of top and bottom pH decrease of M30 culture.

When commercial M30 culture was grown in enzymically treated whey medium and inoculated into skim milk contained in graduated cylinders, rate of acid production at the top of the cylinder improved (P<0.01) over the 5 hour incubation period compared to the same culture grown in the control medium (see FIG. 3 and Table 1). In the cylinders inoculated with the M30 culture grown in control media, top pH decreased only by 0.08 pH units over 5 hour period. This culture agglutinated within the first hour of incubation sinking to the bottom of the cylinders. Acid production at the bottom of the cylinders was rapid as observed by rapid decline in bottom pH of the cylinders (FIG. 3).

When the M30 culture was grown in the enzymically treated media and inoculated into skim milk, pH both at the top and at the bottom of the cylinders decreased at the same rate. The pH differential over 5 hour incubation period was reduced from 0.68 (cultures grown in the control medium) to 0.31 (that grown in enzymically treated medium) (Table 1). The pH differential was decreased ($P<0.01$) by 55% suggesting that culture agglutination was being inhibited and culture performance improved.

Figure 4:
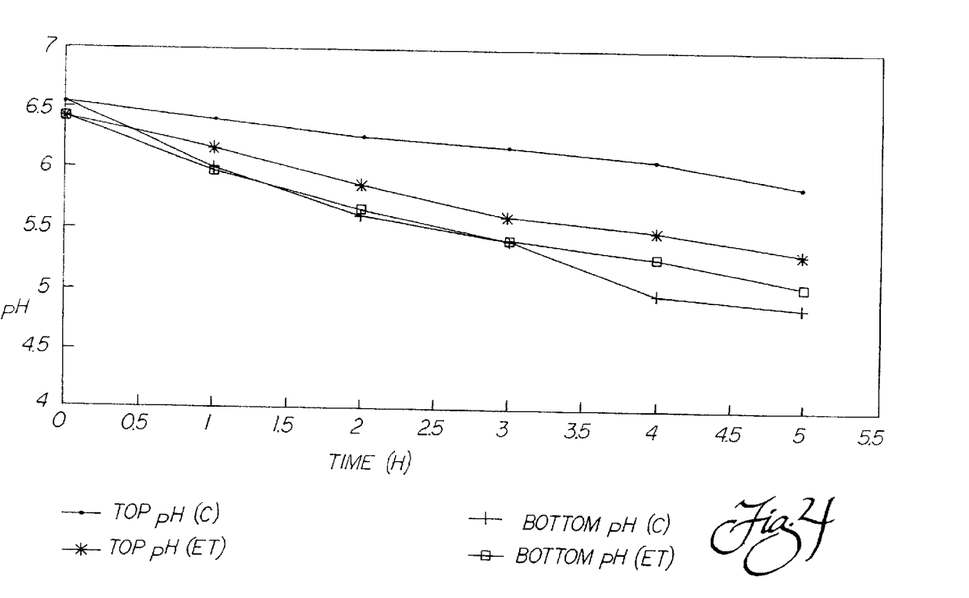
FIG. 4 graphically shows the rate of top and bottom pH decrease of M37 culture.

Among all three commercial cultures studied, M37 showed the greatest improvement: in culture performance when grown in the enzyme treated whey media compare to the control (Table 1 and FIG. 4). When M37 was grown in the control medium and inoculated into skim milk, the rate of acid production at the top of the cylinder was slow. The pH decreased by 0.06 units over 5 hours. Similar to the M30 culture, M37 also agglutinated within the first hour of incubation falling to the bottom of the cylinders. The pH decrease at the bottom of the cylinders was fairly rapid during the 5 hours of incubation (see FIG. 4).

When the M37 culture was grown in the enzymically treated media and inoculated into skim milk a steady decrease in pH was observed at the top and at the bottom of the cylinders over the 5 hours (see FIG. 4). The pH differentials over the 5 hour incubation period decreased from 0.64 for cultures grown in the control medium to 0.18 to that grown in enzymically treated medium (Table 1). The pH differential was reduced ($P<0.01$) by 72% suggesting an inhibition of culture agglutination and improvement of culture performance.

The cylinders were visually inspected at the end of the 5 hours for sediment formation. Cylinders inoculated with M30 and M37 cultures grown in the control medium both had heavy sedimentation (5 and 6 cm deep, respectively) at the bottom of the cylinders. This sediment was greatly reduced when M30 and M37 cultures were grown in the enzyme treated medium. A slight brown tint on the color of the sediment was also observed indicating that little additional casein from skim milk precipitated around the agglutinated cell complexes.

Statistical analysis showed media×culture interaction to be significant ($P<0.01$) for rate of decrease of top and bottom pH and pH differentials. The extent that the culture performance is improved when grown in the enzymically treated whey medium depends somewhat on the specific culture and perhaps is related to the severity of agglutination associated with a particular strain. The severity of agglutination of a particular strain depends on several factors such as the frequency that a specific antigenic determinant is expressed on the cell surface or the agglutinin titer which may indicate an antibody's specificity to a certain cell surface antigenic determinant. Perhaps these factors contributed to the differences observed in this study and the extent of improvement in culture performance of the various commercial cultures investigated.

Culture Morphology:

When Lactococcus cultures agglutinate, long chains or clumps of chains are observed in the sediment formed, whereas nonagglutinating cultures form smaller clumps or no clumps and shorter chains appear more evenly dispersed throughout the skim milk. Photomicrographs of the three cultures grown in the control medium and enzymically treated whey medium showed that all three cultures formed considerable shorter chains and almost no clumping of chains when these cultures were grown in enzymically treated whey medium compared to their controls.

Short chains lacking in critical mass to sink to the bottom of the cylinders are more evenly dispersed throughout the skim milk providing for improved culture performance throughout the cylinder during incubation. Thus improved acid production particularly at the top of the cylinders was observed.

EXAMPLE 2

The procedure set forth in Example 1 is followed except that non-fat dried milk is substituted for rennet whey.

EXAMPLE 3

The procedure set forth in Example 1 is followed except that ficin is substituted for papain.

EXAMPLE 4

The procedure set forth in Example 1 is followed except that raw whey is substituted for rennet whey.

EXAMPLE 5

The procedure set forth in Example 1 is followed except that bromelain is substituted for papain.

EXAMPLE 6

The procedure set forth in Example 1 is followed except that non-fat-dried milk is substituted for rennet whey and ficin is substituted for papain.

EXAMPLE 7

The procedure set forth in Example 1 is followed except that raw whey is substituted for rennet whey and bromelain is substituted for papain.

EXAMPLE 8

*Lactococcus lactis* ssp. *lactis* B62 (Chr. Hansen Laboratories, Milwaukee, Wis.) was propagated from frozen stock cultures in reconstituted (10%) nonfat dry milk. Insure Media (Waterford, Food Products) was prepared (75.8 g/L distilled water) and inoculated (4%) with the propagated culture and incubated at 26° C. overnight.

Five hundred mL aliquots of Beef Plasma (4%) were digested with crude Papain (1%), crude Ficin (0.1%) and crude Bromelain (0.01%) at 26° C. for 2 h. Digested Beef Plasma was ultrafiltered (3000 mwco, Diaflo Ultrafiltration membranes, Amicon, Inc.) at 4° C. Permeates were stored (−10° C.) until media were formulated.

Five Internal pH Controlled bulk starter media were prepared. Media were designed around a commercial lactic medium sold by Waterford Food Products which supplied both an intact medium (Insure™) and the buffering salts (Insure™ salts) used in their intact medium. Two media were prepared from Insure™ medium, one of which would be used in a treatment spiked with purified immunoglobulin (1 g/250 mL). These two media were used as controls. Three media were prepared using the Insure™ salts (0.15 g) plus yeast extract (1%, amount normally in INSURE™ medium) reconstituted with 5 mL of one of three enzyme hydrolyzed permeates. All media were heat treated at 85° C. for 45 min and stored at 4° C. A commercial single strain lactic culture B62 was used to inoculate (50%) these media. All were incubated (26 C) overnight to develop bulk starters.

Nonfat dry milk (8.8%) was reconstituted in distilled water and placed in five (250 mL) graduated glass cylinders. One g of freeze dried, purified immunoglobulin protein was added to one skim milk-containing cylinder. Control culture was added to the cylinder containing the immunoglobulin. The other skim milk containing cylinders were inoculated with the other bulk starters. All skim milks were inoculated with 4% bulk starter. All skim milk-cylinders were incubated at 31° C. for 6 h. pH measurements were determined after inoculation and at 1 h intervals. pH measurements were taken at 5 cm below the surface and on the bottom of each cylinder.

RESULTS

Figure 5:
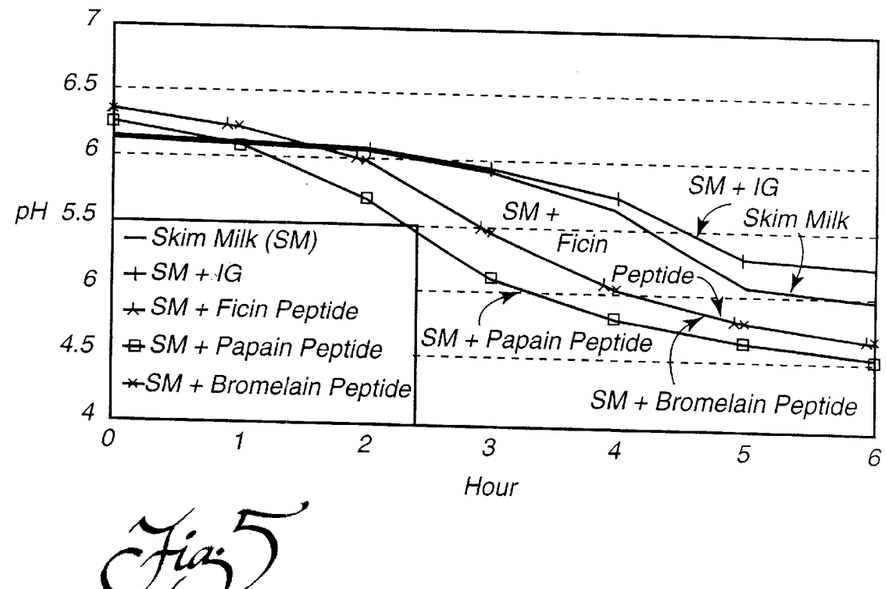
FIG. 5 is a plot of the pH at the top of the skim milk column after addition of immunoglobulin (IgG), ficin derived peptides, papain derived peptides and bromelain derived peptides per example 8.

A plot of the pH at the top of the skim milk column is shown in FIG. 5. As expected the skim milk containing the added immunoglobulin had the slowest drop in pH. This is because the immunoglobulin enhances culture agglutination, that causes the cells to clump together and fall to the bottom of the cylinder. Since most of the culture was on the bottom of the cylinder the acid development in the top of the skim milk column was limited to the culture remaining in solution. The skim milk containing the other control culture was the second slowest in developing acid in the top of the cylinder. Evidently, sufficient immune proteins were present in the skim milk to cause the culture to agglutinate and drop to the bottom of the cylinder. However, not as many culture cells dropped in this skim milk as did in the skim milk that contained the added immunoglobulin.

All three skim milk's that were inoculated with culture grown in media that contained peptides developed acid in the top of the skim milk column faster ($p<0.001$) than the controls. Also note that the bulk starters that contained the peptides did not drop the initial pH of the skim milk as much as the control media. Evidently peptides derived from blood serum protected the culture from agglutinating and more of the culture remained in solution. Culture grown in the medium containing peptides produced by papain appeared to be the most protected. The pH of this skim milk dropped faster than the skim milk that contained the cultures that were grown in the media containing the ficin and bromelain peptides.

The pH differentials (difference between the top and bottom pH of the skim milk after four hours of incubation) is shown in Table 2. Differentials result when culture cells drop to the bottom of the cylinder. The lactic cells on the bottom are more numerous and therefore produce more acid than those throughout the body of the skim milk. Note that the cultures grown in the media containing peptides had a lower differential than the controls.

TABLE 2

Effect of culture media on pH differentials in skim milk after 4 h of incubation.

| Culture Medium | pH differential |
|---|---|
| Insure | .51 |
| Insure + Immunoglobulin | .56 |
| Insure salt + Ficin peptide | .46 |
| Insure salt + Papain peptide | .32 |
| Insure salt + Bromelain peptide | .37 |

It is evident from Examples 1–7 that culture agglutination protective blockers can be cut from milk sources or from blood serum as shown in this example. Indeed any source of material that contains immunoglobulin may be used as a starting material to produces these peptides.

EXAMPLE 9

The procedure set forth in claim 8 is followed except that a purified immune protein preparation is substituted for the digested beef plasma.

EXAMPLE 10

Often women can not become pregnant because their immune system (immuno-proteins IgM, IgG and IgA) attacks the spermatozoa. The Immuno-proteins bind to antigenic sites located on the surface of the sperm cell. These immuno-proteins also bind to each other (complimentary binding). As the immuno-proteins bind to antigenic sites on the sperm surface a conformation shift occurs allowing complimentary binding to occur, thus chains of immune proteins form bridges between sperm cells causing the cells to agglutinate. Agglutination inhibits spermatozoa mobility, thus they are unable to travel far enough to find and fertilize the female egg. The purpose of this project was to find a way to inhibit spermatozoa agglutination.

Materials and Methods

Preparation of peptide blockers. Peptide blockers were prepared from sweet whey which had been hydrolyzed with papain at 28° C. During the hydrolyzation process peptides were collected by pumping the hydrolysate through a 10,000 MW cut off polysulfone ultrafiltration membrane. Permeate from the membrane was freeze dried to concentrate the collected peptides.

Preparation of blood serum. Bovine blood was collected at the time of slaughter. The blood was allowed to coagulate while cooling to 2° C. Coagulated blood was stirred and centrifuged at 5000×g for 10 min. Serum from each centrifuge tube was carefully removed and stored in 1 and 2 ml cryo-vials. Cryovials were frozen at −20° C. until the serum was used.

Preparation of spermatozoa. Human spermatozoa were washed in TEST buffer (1/1 ratio), centrifuged (50,000×g) and resuspended in TEST buffer to their original volume. A reaction mixture was prepared from 5 ml of washed spermatozoa, with and without 10 mg peptide blockers, and either 0.4 or 0.5 ml Bovine blood serum. Spermatozoa were monitored at 0,1, 5, 10, 15, 20, 25, 30 min. to determine the number of active cells, motility, and grade.

Agglutination determination. Spermatozoa from reaction mixtures were placed (0.05 ml) on a warmed (38° C.) slide and covered with a cover slip. The slide was placed an a warmed microscope table (38° C.) and viewed at 100×. Slides (Ektachrome 5017, ASA 100) were taken at all observations times.

Total sperm cell numbers were determined using direct microscopic observation techniques using a calibrated slide. Number of free cells were determined from the slides by counting the free sperm cells that were not in clumps. Total free sperm cell counts /ml were then computed from the area ratio of the calibration slide.

Mobility was determined by a trained technician who estimated the number of spermatozoa that were actually moving using a scale of 0 to 100. Grade of spermatozoa (how well they move) was also determined by the same technician using a scale of 1 to 4.

Results and Discussion

Agglutination model. The model used to determine agglutination of human sperm cells was designed to cause the spermatozoa to agglutinate within a short time interval (approximately 10 min). This model was considered to be an extremely harsh environment for normal sperm cells. Typically sperm cells would not encounter this concentration of immuno-protein or blood serum. Also this model used a different sperm donor each day, therefore the variability between sperm sources to agglutination was considered to be maximized.

Figure 6:
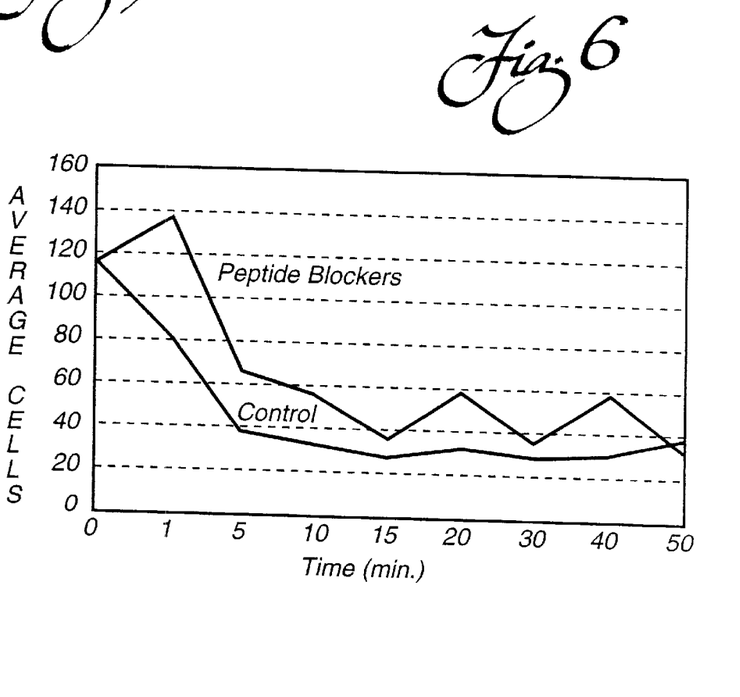
FIG. 6 graphically shows free swimming sperm cells in control and papain derived peptide treated spermatozoa samples per Example 10.

Free spermatozoa. More free cells of spermatozoa were observed ($P<0.05$) in samples containing peptide blockers than samples which did not contain peptide blockers (FIG. 6). Both blocked and unblocked spermatozoa reaction mixtures started out with approximately $400\times10^5$ free swimming cells. Free swimming cells decrease ($P<0.0001$) with time in both blocked and unblocked reactions. The reaction mixture containing peptide blockers averaged $300\times10^5$ free cells, while the sample without peptide blockers averaged $200\times10^5$ free swimming cells, a difference of nearly $100\times10^5$ cells/ml. After incubating the reaction mixtures for 10 minutes, sperm cell agglutination abated and little new sperm cell agglutination occurred when reaction mixtures contained 0.5 ml of blood serum. Sperm cell differentials between blocked and unblocked reaction mixtures between 10 and 20 min averaged $70\times10^5$ cell/ml.

Spermatozoa mobility. Experiments observing spermatozoa mobility were conducted in reaction S mixtures containing both 0.4 and 0.5 ml of blood serum. Results presented in FIG. 3, show that reaction mixtures containing peptide blockers had a greater mobility than those without blockers.

TABLE 3

| | Time (min) | | | | | | | | |
|---|---|---|---|---|---|---|---|---|---|
| TRTS | 0 | 1 | 5 | 10 | 15 | 20 | 35 | 40 | 50 |
| Motility (%) | | | | | | | | | |
| W/PB | 58 | 58 | 58 | 50 | 57 | 51 | 50 | 50 | 50 |
| W/O PB | 50 | 48 | 48 | 37 | 40 | 10 | 5 | 5 | 5 |
| Control | 70 | 70 | 70 | 70 | 70 | 70 | 70 | 70 | 70 |
| Grade (0–4) | | | | | | | | | |
| W/PB | 3.5 | 3.5 | 3.5 | 3.3 | 3.3 | 3.3 | 3.3 | 3.2 | 3.0 |
| W/O PB | 3.3 | 3.3 | 3.3 | 3.0 | 3.0 | 0 | 0 | 0 | 0 |
| Control | 3.5 | 3.5 | 3.5 | 3.5 | 3.5 | 3.5 | 3.5 | 3.5 | 3.5 |

The results obtained in this study indicate that the presence of peptides blockers reduced the incidence of agglutination and higher numbers of "free" spermatozoa exhibited levels of motility and grade of motility ($P<0.05$). Significant agglutination occurred after 10 minutes of incubation.

Conclusions: Spermatozoa incubated with TEST media in the presence of peptide blockers were immunoprotected from the immune proteins present in bovine blood serum. The qualative characteristics of these spermatozoa suggest that peptide blockers can be a useful mode of immunoprotecting spermatozoa during semen preparation and more importantly after the placement of the spermatozoa inside the female reproductive tract.

EXAMPLE 11

Modulated differential scanning calorimetry (TA instruments, Model DSC 2920) was performed to thermally analyze Bovine IgG (reagent grade), hydrolyzed whey peptides and lactose (anhydrous). Peptides were separated from papain hydrolyzed whey by ultrafiltration (10,000 mwco polysulfone membrane) and freeze dried. Empty aluminum reference and sample pans were paired to ±0.5 mg. Samples were weighted (1.7 mg IgG, 4 mg peptide, 0.4 mg lactose) in the sample pan and skim milk ultrafiltrate buffer was added by micro-pipette (to 100 $\mu$L volume). Samples were dissolved by stirring with a micro-spatula. Sample and reference (empty) pans were hermetically sealed. Calorimetry measurements were conducted (30 to 150° C.) with modulation amplitude of 0.531° C./100 sec and ramp gradient of 2° C./min.

Thermal analysis of IgG revealed major heat flows followed non-reversing heat flows by approximately 1° C. at peaks of 74, 104 and 119 to 123° C. A heat capacity shift was noted at 104° C. Minor non-reversing heat flows occurred at 48 to 49, 54 to 55 and 88 to 90° C.

The freeze dried fraction contained both lactose and peptides. Lactose produced extremely linear heat flow curves that did not appear to interfere with thermal analysis of the peptide fraction. Fractionated whey peptides contained 2 sulfur linkages that broke at peaks of 119 to 124° C. Other heat flow patterns from whey peptides started and peaked at 46.0 and 51.8, respectively, and 87.9 and 94.2° C., respectively. These heat flows appeared to align with two minor heat flow areas observed in IgG but not with the major heat flow area. Although modulated differential scanning calorimetry cannot be used to identify a parent molecule it can be used to identify disulfide bonds and structural characteristics that are apparent in both molecules. This data is consistent and supports the observations that the active whey peptide are derived from immue proteins such as IgG.

In summary, numerous benefits have been described which result from employing the concepts of the present invention. A novel method has been described that is particularly useful in inhibiting the binding activity of immunoglobulins for a particular immunogen. Specifically, the immunogen is treated with the inhibitor so as to block antigenic sites or determinants that otherwise would be the target of immunoglobulin binding activity. Such a methodology has a number of applications and is useful in virtually all instances where problematic immune reactions would otherwise occur. Such applications include but are not limited to improving the efficiency and effectiveness of the cheese making process and artificial insemination techniques while protecting the spermatozoa from host antibody attack.

The invention has been described herein with reference to certain preferred methods and binding activity inhibitors. However, as it is obvious that variations thereon will become apparent to those skilled in the art, the invention is not to be considered as limited thereto.

What is claimed is:

1. A method for inhibiting culture agglutination in a fermentation medium including immunoglobulins, comprising the steps of:

contacting an immunoglobulin selected from the group consisting of IgA, IgG, IgM and mixtures thereof with a plant protease selected from the group consisting of papain, ficin, bromelain and mixtures thereof to hydrolyze the immunoglobulin, thereby forming a composition comprised of immunoreactive peptides;

submitting the composition comprising immunoreactive peptides to ultrafiltration and recovering and collecting immunoreactive peptides having a molecular weight of less than 10,000 Daltons;

adding to a nutrient growth medium for a Lactococcus useful in a fermentation process an amount of the collected immunoreactive peptides of a molecular weight of less than 10,000 Daltons effective to bind antigenic sites on the Lactococcus;

innoculating said nutrient growth medium with the Lactococcus useful in a fermentation process and growing said Lactococcus in the nutrient growth medium until antigenic sites on the Lactococcus are bound and blocked with immunoreactive peptides of a molecular weight of less than 10,000 Daltons;

transferring the proliferated Lactococcus having antigenic sites blocked to a fermentation medium wherein immunoglobulins comprised in the fermentation medium cannot bind the antigenic sites on the Lactococcus blocked by immunoreactive peptides of a molecular weight of less than 10,000 Daltons;

whereby agglutination of the Lactococcus in the fermentation medium is inhibited.

2. The method as set forth in claim 1, wherein said immunoreactive peptides have a molecular weight of about 1,000 Daltons.

3. The method set forth in claim 1, wherein said immunoglobulin is provided from a source selected from the group consisting of raw whey, dried whey, whey protein isolates, non-fat-dried milk, blood serum protein isolates, purified immune protein preparations and mixtures thereof.

4. A method for inhibiting culture agglutination in a fermentation medium including immunoglobulins, comprising the steps of:

contacting an immunoglobulin selected from the group consisting of IgA, lgG, IgM and mixtures thereof with a plant protease selected from the group consisting of papain, ficin, bromelain and mixtures thereof to hydrolyze the immunoglobulin, thereby forming a composition comprised of immunoreactive peptides;

submitting the composition comprising immunoreactive peptides to diafiltration and recovering and collecting immunoreactive peptides having a molecular weight of less than 10,000 Daltons;

adding to a nutrient growth medium for a Lactococcus useful in a fermentation process an amount of the collected immunoreactive peptides of a molecular weight of less than 10,000 Daltons effective to bind antigenic sites on the Lactococcus; innoculating said nutrient growth medium with the Lactococcus useful in a fermentation process and growing said Lactococcus in the nutrient growth medium until antigenic sites on the Lactococcus are bound and blocked with immunoreactive peptides of a molecular weight of less than 10,000 Daltons;

transferring the proliferated Lactococcus having antigenic sites blocked to a fermentation medium wherein immunoglobulins comprised in the fermentation medium cannot bind the antigenic sites on the Lactococcus blocked by immunoreactive peptides of a molecular weight of less than 10,000 Daltons;

whereby agglutination of the Lactococcus in the fermentation medium is inhibited.

5. The method as set forth in claim 4, including adding a buffer to the composition comprising immunoreactive peptides at the same rate as the immunoreactive peptides are collected.

6. The method as set forth in claim 4, wherein the immunoglobulin is contacted with the plant protease at a temperature between 30–50° C. for a period of time of at least two hours.

* * * * *